United States Patent
Sendai

(10) Patent No.: US 7,127,028 B2
(45) Date of Patent: Oct. 24, 2006

(54) RADIATION IMAGE TAKING SYSTEM

(75) Inventor: Tomonari Sendai, Kanagawa-ken (JP)

(73) Assignee: Fuji Photo Film Co., Lts., Kanagawa-ken (JP)

(*) Notice: Subject to any disclaimer, the term of this patent is extended or adjusted under 35 U.S.C. 154(b) by 0 days.

(21) Appl. No.: 11/086,445

(22) Filed: Mar. 23, 2005

(65) Prior Publication Data

US 2005/0213701 A1    Sep. 29, 2005

(30) Foreign Application Priority Data

Mar. 23, 2004  (JP)  ............... 2004-085109
Sep. 14, 2004  (JP)  ............... 2004-266753

(51) Int. Cl.
H05G 1/60 (2006.01)
H05G 1/10 (2006.01)

(52) U.S. Cl. ............... 378/21; 378/23; 378/95; 378/155

(58) Field of Classification Search ............... 378/4, 378/7–9, 19–25, 98.8, 154, 155, 94, 95
See application file for complete search history.

(56) References Cited

U.S. PATENT DOCUMENTS

| 6,181,773 | B1* | 1/2001 | Lee et al. ............... 378/155 |
| 6,904,119 | B1* | 6/2005 | Oikawa ............... 378/15 |
| 6,970,531 | B1* | 11/2005 | Eberhard et al. ............. 378/26 |
| 2004/0136490 | A1* | 7/2004 | Edic et al. ............... 378/4 |

FOREIGN PATENT DOCUMENTS

JP    2003-250790 A    9/2003

* cited by examiner

Primary Examiner—Edward J. Glick
Assistant Examiner—Irakli Kiknadze
(74) Attorney, Agent, or Firm—Sughrue Mion, PLLC

(57) ABSTRACT

A tomosynthetic image taking apparatus takes an x-ray image of an object in each of a plurality of positions of an x-ray source to obtain a desired tomogram of the object by adding up the x-ray images thus obtained. A heartbeat phase is detected and the tomosynthetic image taking apparatus is controlled to take an x-ray image of the object in each of the plurality of positions of the x-ray source when the heartbeat of the object is in the same heartbeat phase.

12 Claims, 14 Drawing Sheets

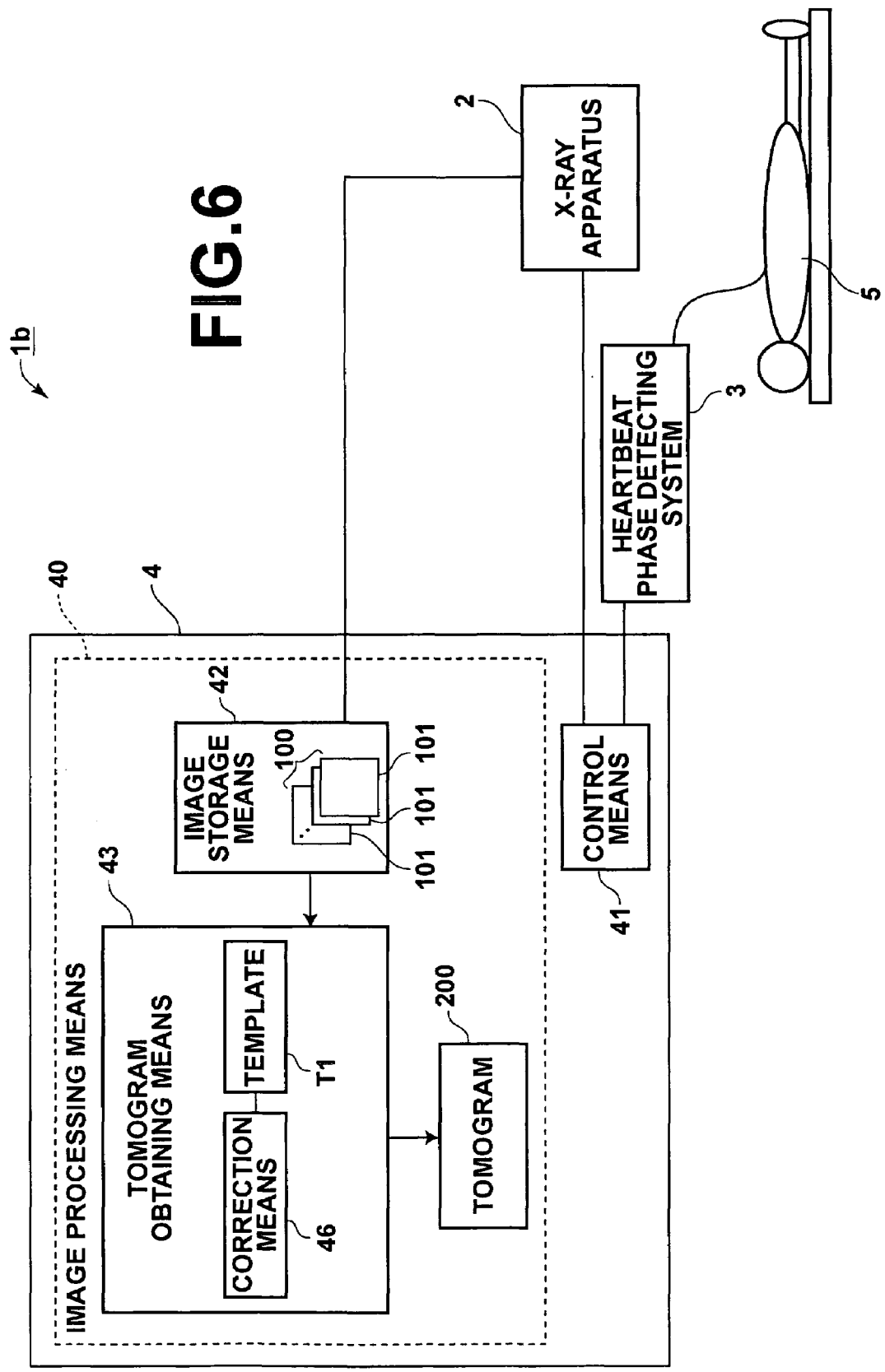

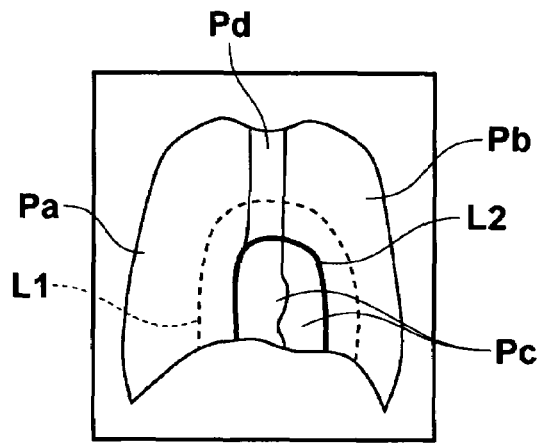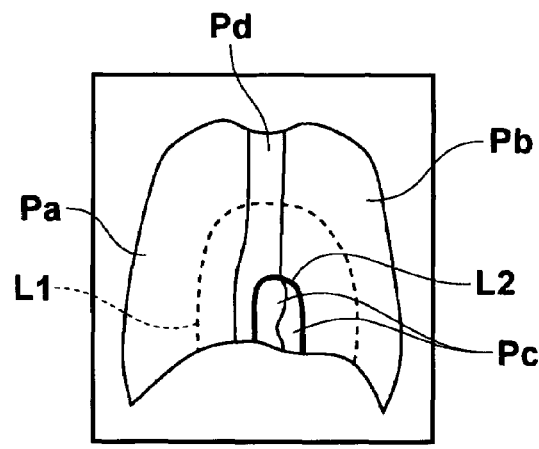
FIG.10A  FIG.10B
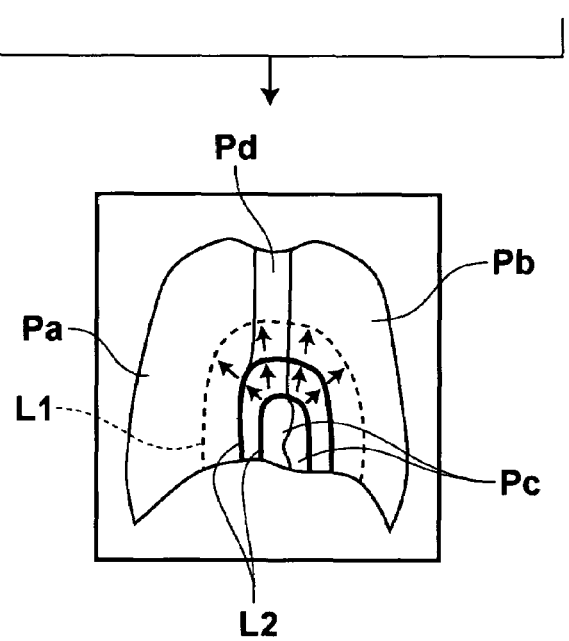
FIG.10C

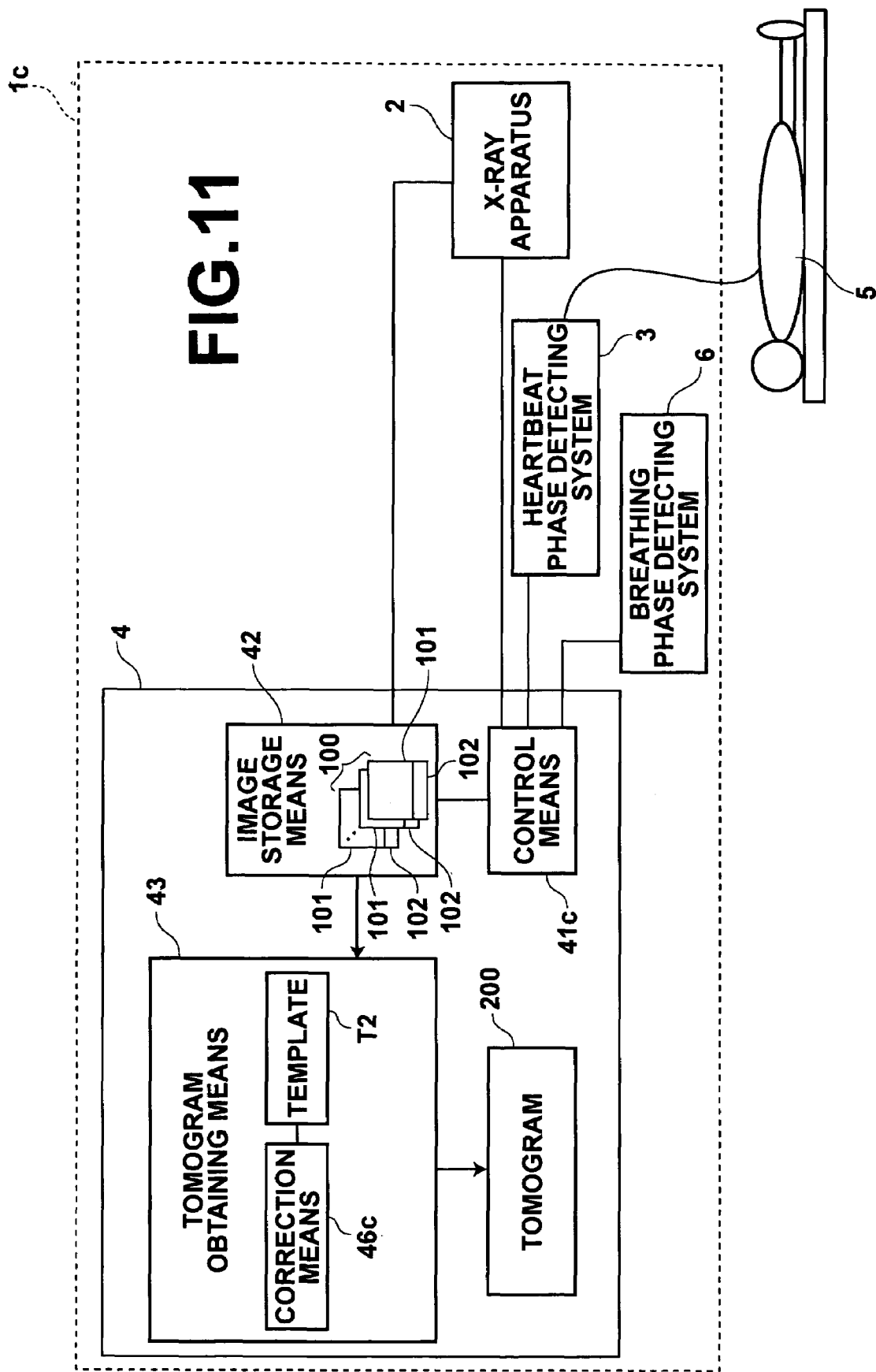

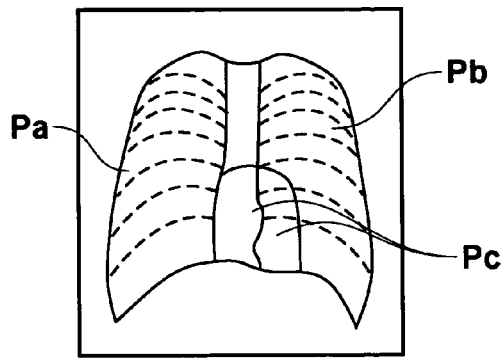
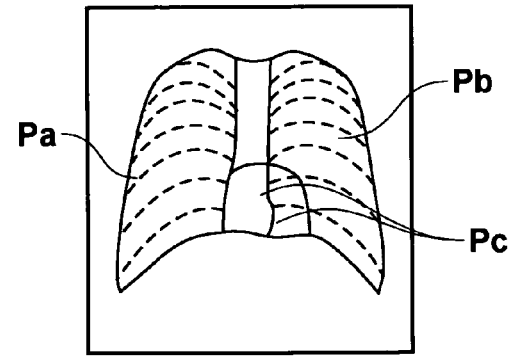
FIG.13A  FIG.13B
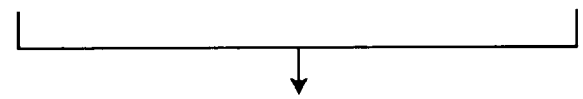
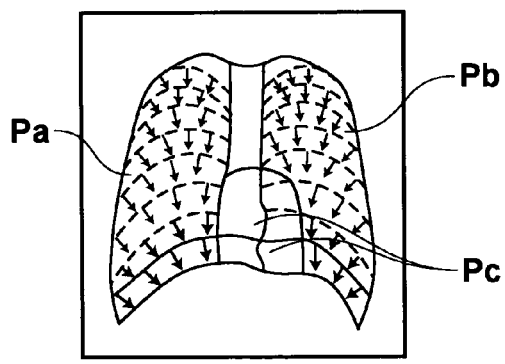
FIG.13C

RADIATION IMAGE TAKING SYSTEM

BACKGROUND OF THE INVENTION

1. Field of the Invention

This invention relates to tomosynthesis for obtaining a tomogram from x-rays, and more particularly to an x-ray system for obtaining a tomogram of the chest.

2. Description of the Related Art

In order to observe the diseased part, there has been carried out comparison between an x-ray image which was taken in the past and an x-ray image which was currently taken. Upon comparison between a past x-ray image (an x-ray image which was taken in the past) and a current x-ray image (an x-ray image which was currently taken), it is not easy to grasp the difference between the past x-ray image and the current x-ray image, for instance, when the past x-ray image was taken during shrinkage of the heart and the current x-ray image was taken during expansion of the heart since a state where the lung is inflated and a state where the lung is compressed and deformed are compared with each other. Accordingly, it has been proposed to detect the cycle of the heartbeat by measuring shrinkage and expansion of the heart by the use of an electrocardiograph, a sphygmograph or the like and take an x-ray image constantly during shrinkage of the heart. (See, for instance, Japanese Unexamined Patent Publication No. 2003-250790)

Further, tomosynthesis where the x-ray tube is moved to take x-ray images at different angles and the obtained images are added to obtain an image where a desired cross-section is enhanced is recently proposed in the CR (computed radiography) in order to observe the diseased part in more detail.

In the tomosynthesis, the x-ray tube is moved in parallel to a flat panel or along a circular or elliptical path to take x-ray images at different angles and the x-ray images are reconstructed to obtain a tomogram. A method of reconstructing the x-ray images to obtain a tomogram will be described, hereinbelow.

When the x-ray tube is moved to positions S1, S2, ... Sn to take images of an object body 5 at different angles, different x-ray images I1, I2, .... In are obtained as shown in FIG. 1. When, for instance, x-rays are projected from the position S1 of the x-ray source onto two object parts (01 and 02) at different depths, images of the object parts (01, 02) are formed in positions P11 and P12 of the x-ray images I1, whereas, when x-rays are projected from the position S2 of the x-ray source onto the object parts (01 and 02), images of the object parts (01, 02) are formed in positions P21 and P22 of the x-ray images I2. When x-rays are repeatedly projected from the different positions of the x-ray source S1, S2, ... Sn onto the object parts (01 and 02) in this manner, images of the object parts (01) are formed in positions P11, P21, ... Pn1, and images of the object parts (02) are formed in positions P12, P22, ... Pn2.

When the cross-section where the object part 01 exists is to be enhanced, the x-ray image I2 is shifted by a distance equal to the distance between P21 and P11, the x-ray image I3 is shifted by a distance equal to the distance between P31 and P11, ... and the x-ray image In is shifted by a distance equal to the distance between Pn1 and P11, and the images thus obtained are added up, whereby a tomogram where the structure on the cross-section at the depth of the object part 01 is enhanced is created. When the cross-section where the object part 02 exists is to be enhanced, the x-ray image I2 is shifted by a distance equal to the distance between P22 and P12, the x-ray image I3 is shifted by a distance equal to the distance between P32 and P12, ... and the x-ray image In is shifted by a distance equal to the distance between Pn2 and P12, and the images thus obtained are added up. Thus by adding up the images obtained by shifting the x-ray images I1, I2, ..... In to be aligned with each other depending on the position of a desired cross-section, an image where a tomogram in a desired position is enhanced can be obtained.

By observing a tomogram obtained by the tomosynthesis, more detailed information can be obtained. However, when a tomogram of the chest is obtained by taking an image of the chest by the tomosynthesis, a light shadow such as of lung cancer sometimes does not appear in the tomogram by a motion artifact due to the heartbeat or the breathing.

When the heartbeat is detected and x-ray images are taken at the same period at the timing of shrinkage of the heart as in Japanese Unexamined Patent Publication No. 2003-250790, though the comparison between the past x-ray image and the current x-ray image is facilitated, the accuracy at which a light shadow such as of lung cancer can be recognized cannot be improved.

SUMMARY OF THE INVENTION

In view of the foregoing observations and description, the primary object of the present invention is to provide a radiation image taking system in which, for instance, an abnormal shadow which appears in the image of the chest can be detected at a high accuracy.

In accordance with a first aspect of the present invention, there is provided a radiation image taking system comprising a tomosynthetic image taking means which takes an x-ray image of an object in each of a plurality of positions of an x-ray source to obtain a desired tomogram of the object by adding up the x-ray images thus obtained, a heartbeat phase detecting means which detects the heartbeat phase of the object, and a tomosynthesis control means which controls the tomosynthetic image taking means to take an x-ray image of the object in each of the plurality of positions of the x-ray source when the heartbeat of the object detected by the heartbeat phase detecting means is in the same heartbeat phase.

The "heartbeat phase" means the position in the cycles of the heartbeat formed by shrinkage and expansion of the heart.

As the "heartbeat phase detecting means", for instance, an electrocardiograph and a sphygmograph may be used.

In accordance with a second aspect of the present invention, there is provided a radiation image taking system comprising a tomosynthetic image taking means which takes an x-ray image of an object in each of a plurality of positions of an x-ray source to obtain a desired tomogram of the object by adding up the x-ray images thus obtained, a heartbeat phase detecting means which detects the heartbeat phase of the object, an breathing phase detecting means which detects the breathing phase of the object, and a tomosynthesis control means which controls the tomosynthetic image taking means to take an x-ray image of the object in each of the plurality of positions of the x-ray source when the heartbeat of the object detected by the heartbeat phase detecting means is in the same heartbeat phase and when the breathing of the object detected by the breathing phase detecting means is in the same breathing phase.

The "tomosynthetic image taking" means to obtain a tomogram of a particular cross-section of the object by taking x-ray images while changing the angles at which the x-rays are projected onto the object.

The "breathing phase" means the position in the cycles of the breathing formed by the expiration and the aspiration.

As the "breathing phase detecting means", for instance, a means which detects the breathing phase of the object by monitoring breathing of the object by the use of a spirometer, a breathing monitor belt and/or an optical camera may be used.

In accordance with a third aspect of the present invention, there is provided a radiation image taking system comprising a tomosynthetic image taking means which takes an x-ray image of an object in each of a plurality of positions of an x-ray source to obtain a desired tomogram of the object by adding up the x-ray images thus obtained, a heartbeat phase detecting means which detects the heartbeat phase of the object, an breathing phase detecting means which detects the breathing phase of the object, a tomosynthesis control means which controls the tomosynthetic image taking means to take an x-ray image of the object in each of the plurality of positions of the x-ray source when the heartbeat of the object detected by the heartbeat phase detecting means is in the same heartbeat phase, and a correction means which corrects at least a part of the plurality of the images taken in the plurality of positions of the x-ray source so that they are all in the same breathing phase on the basis of the breathing phases detected by the breathing phase detecting means when the images are taken.

The "tomosynthetic image taking means" may have a scattering radiation removing grid and a grid moving means which moves the scattering radiation removing grid, and the "tomosynthesis control means" may control the grid moving means so that the moving speed of the scattering radiation removing grid is maximized when the x-ray image of the object is taken.

In accordance with a fourth aspect of the present invention, there is provided a radiation image taking system comprising a tomosynthetic image taking means which takes an x-ray image of an object in each of a plurality of positions of an x-ray source to obtain a desired tomogram of the object by adding up the x-ray images thus obtained, a heartbeat phase detecting means which detects the heartbeat phase of the object, a storage means which stores the x-ray image of the object taken in each of the plurality of positions of the x-ray source, and a correction means which corrects at least a part of the plurality of the images taken in the plurality of positions of the x-ray source so that they are all in the same heartbeat phase on the basis of the heartbeat phases detected by the heartbeat phase detecting means when the images are taken.

In accordance with a fifth aspect of the present invention, there is provided a radiation image taking system comprising a tomosynthetic image taking means which takes an x-ray image of an object in each of a plurality of positions of an x-ray source to obtain a desired tomogram of the object by adding up the x-ray images thus obtained, a heartbeat phase detecting means which detects the heartbeat phase of the object, an breathing phase detecting means which detects the breathing phase of the object, a storage means which stores the x-ray image of the object taken in each of the plurality of positions of the x-ray source, and a correction means which corrects at least a part of the plurality of the images taken in the plurality of positions of the x-ray source so that they are all in the same heartbeat phase and in the same breathing phase on the basis of the heartbeat phases detected by the heartbeat phase detecting means when the image is taken and the breathing phases detected by the breathing phase detecting means when the image is taken.

The "tomosynthetic image taking means" may have a scattering radiation removing grid and a grid moving means which moves the scattering radiation removing grid, and the "tomosynthesis control means" may control the grid moving means so that the moving speed of the scattering radiation removing grid is maximized when the x-ray image of the object is taken.

In accordance with a sixth aspect of the present invention, there is provided a computer program for causing a computer to execute the steps of reading out x-ray images of an object each of which is taken in a plurality of positions of an x-ray source and which can provide a desired tomogram of the object by adding up them, and heartbeat information representing the heartbeat phase of the object when the x-ray images are taken, and correcting at least a part of the plurality of the images taken in the plurality of positions of the x-ray source so that they are all in the same breathing phase on the basis of the breathing phases of the object when the images are taken.

In accordance with a seventh aspect of the present invention, there is provided a computer program for causing a computer to execute the steps of reading out x-ray images of an object each of which is taken in a plurality of positions of an x-ray source and which can provide a desired tomogram of the object by adding up them, and heartbeat information and breathing information respectively representing the heartbeat phase and the breathing phase of the object when the x-ray images are taken, and correcting at least a part of the plurality of the images taken in the plurality of positions of the x-ray source so that they are all in the same breathing phase and in the same heartbeat phase on the basis of the breathing phases and the heartbeat phase of the object when the images are taken.

In accordance with the present invention, since a tomogram is obtained by taking a tomosynthetic image so that the x-ray images taken in a plurality of positions of the x-ray source are coincide with each other in the heartbeat phase, a light shadow such as of lung cancer near the heart does not disappear in the tomogram due to influence of the heart motion and the chest can be observed in detail.

Further, by obtaining a tomogram by taking a tomosynthetic image so that the x-ray images taken in a plurality of positions of the x-ray source are coincide with each other in the heartbeat phase and the breathing phase, a light shadow such as of lung cancer near the heart does not disappear in the tomogram due to influence of the heart motion and the chest can be observed in detail.

Further, by obtaining a tomogram by taking a tomosynthetic image so that the x-ray images taken in a plurality of positions of the x-ray source are coincide with each other in the heartbeat phase and correcting them so that they are all in the same breathing phase, a tomogram where a light shadow such as of lung cancer appears can be obtained and the chest can be observed in detail even if the object keeps breathing without holding his or her breath during taking the x-ray images.

Further, even if the x-ray images taken in a plurality of positions of the x-ray source when taking a tomosynthetic image are not coincide with each other in the heartbeat phase, a tomogram where a light shadow such as of lung cancer appears can be obtained and the chest can be observed in detail by correcting them so that they are all in the same heartbeat phase.

Further, even if the x-ray images taken in a plurality of positions of the x-ray source when taking a tomosynthetic image are coincide with each other neither in the heartbeat phase nor in the breathing phase, a tomogram where a light shadow such as of lung cancer appears can be obtained and the chest can be observed in detail by correcting them so that they are all in the same heartbeat phase and in the same breathing phase.

Further, by taking the x-ray images by the use of the scattering radiation removing grid and controlling the scattering radiation removing grid so that the moving speed of the scattering radiation removing grid is maximized when the x-ray image of the object is taken, a tomogram where the scattering radiation is cut and the grid line is prevented from being superimposed can be obtained.

BRIEF DESCRIPTION OF THE DRAWINGS

FIG. 6 is a schematic view showing a basic arrangement of a radiation image recording system in accordance with a third embodiment of the present invention, FIGS. 10A to 10C are views for illustrating a method of correction to conform the heartbeat phases, FIG. 11 is a schematic view showing a basis arrangement of a radiation image recording system in accordance with a fourth embodiment of the present invention, FIGS. 13A to 13C are views for illustrating a method of correction to conform the breathing phases.

DESCRIPTION OF THE PREFERRED EMBODIMENTS

Figure 2:
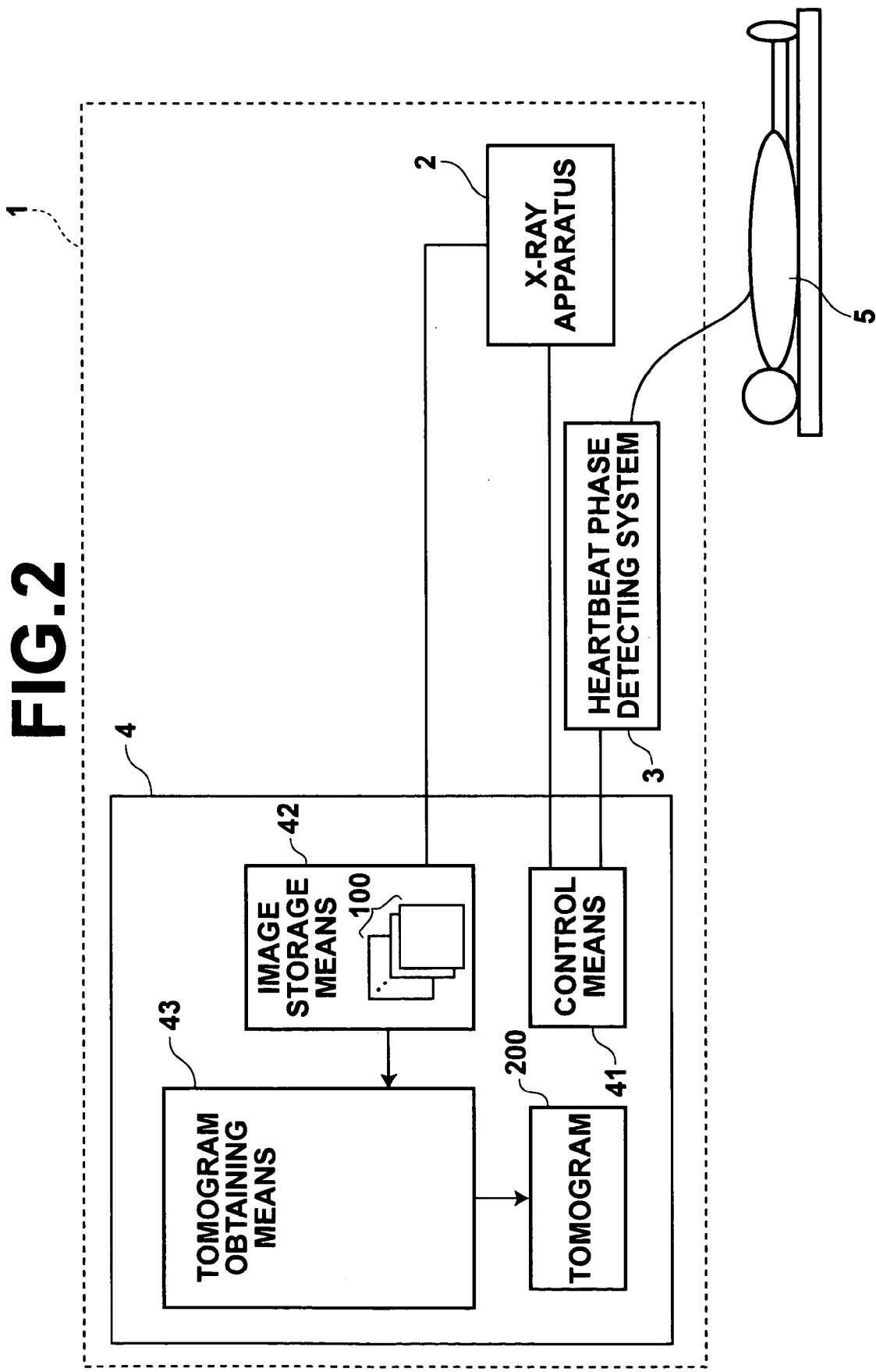
FIG. 2 is a schematic view showing a basic arrangement of a radiation image recording system in accordance with a first embodiment of the present invention.

In FIG. 2, a radiation image recording system 1 in accordance with a first embodiment of the present invention comprises an x-ray apparatus (tomosynthetic image taking apparatus) 2 such as CR which takes an x-ray image of an object 5 in each of a plurality of positions of an x-ray source, a heartbeat phase detecting system (heartbeat phase detecting means) 3 which detects the heartbeat phase of the object 5, and a computer 4 which controls the image taking timing of the x-ray apparatus 2.

The computer 4 comprises a control means 41 which controls the image taking timing of the x-ray apparatus 2, an image storage means 42 which stores the x-ray image 100 taken by the x-ray apparatus 2 in each of the plurality of positions of the x-ray source, and a tomogram obtaining means 43 which obtains a tomogram 200 of the object 5 by adjusting the positions of the x-ray images 100 according to the depth of a necessary cross-section and adding up the x-ray images 100.

Figure 1:
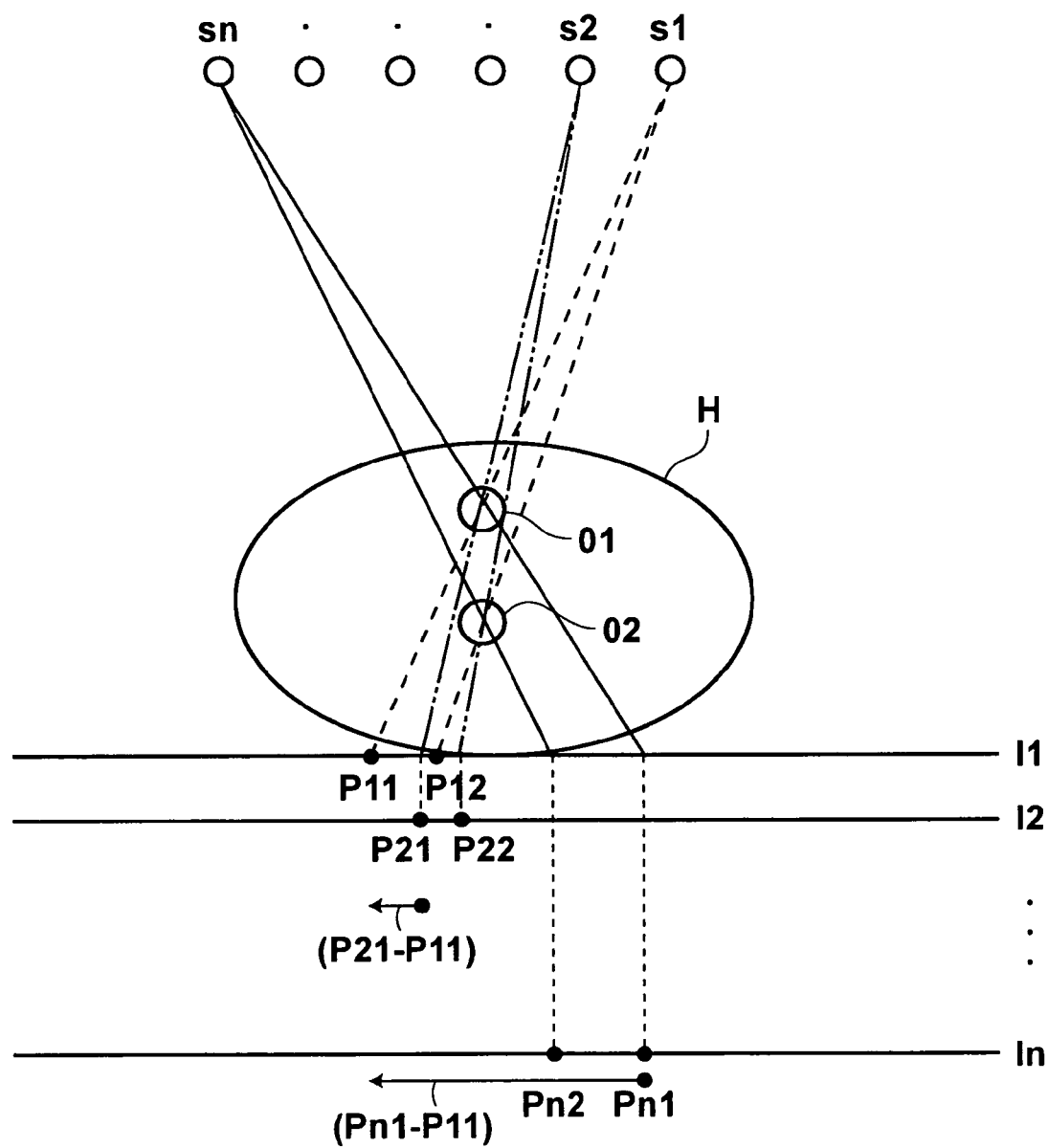
FIG. 1 is a view for illustrating the tomosynthesis.

The x-ray apparatus 2 can move its x-ray tube to positions S1, S2, . . . Sn to take x-ray images of the object 5 at different angles as shown in FIG. 1 so that a tomogram 200 of the object 5 can be obtained.

The control means 41 is connected to the heartbeat phase detecting system 3 to receive the heartbeat phase of the object 5 in real time and makes an instruction of taking an x-ray image of the object 5 by outputting an X-ray generating signal to the x-ray apparatus 2 in the same heartbeat phase of the object 5 when the x-ray tube thereof is in each of the positions S1, S2, . . . Sn.

The image storage means 42 may be a mass storage such as a hard disc built in the computer 4 or a memory of the computer 4 and receives a plurality of x-ray images of the object 5 taken by the x-ray apparatus 2 therefrom to store them as the images 100. Otherwise, the images 100 may be stored in a portable memory such as a DVD and then transferred to the image storage means 42 or may be stored in a file server connected to the x-ray apparatus 2 by way of a network so that the images 100 of a desired object 5 are retrieved in the file server and transferred to the image storage means 42.

The heartbeat phase detecting system 3 may comprise an electrocardiograph and a sphygmograph and detects in analog signal the heartbeat phase of the object 5 formed by shrinkage and expansion of the heart. Then the heartbeat phase detecting system 3 digitizes the analog signal representing the heartbeat phase of the object 5 and transmits it to the control means 41 in real time.

A flow where x-ray images 100 of the chest of the object 5 are taken in the plurality of positions of the x-ray source when the heartbeat of the object 5 is in the same heartbeat phase will be described, hereinbelow.

When an image of the chest is to be taken, the image is generally taken with the object 5 holding his or her breath after he or she takes a large breath to inflate the lung. However it is impossible to hold the heartbeat. Accordingly, in order to take x-ray images 100 of the chest of the object 5 in the same heartbeat phase in each of the plurality of positions of the x-ray source, the heartbeat phase of the object 5 must be detected. For this purpose, the heartbeat phase detecting system 3 is mounted on the object 5.

However, when the sensor of the electrocardiograph is mounted on the chest of the object 5, the sensor opposes the x-raying of the chest of the object 5. Accordingly, it is preferred that the sensor of the electrocardiograph be attached to the object 5 on its arm or leg or the part other than the chest. Further, the sphygmograph includes various types such as a photoelectric type, a piezoelectric type, a pulse-oxy meter type, an acceleration type and the like. Accordingly, when the chest of the object 5 is to be x-rayed with the heartbeat phase detected by the sphygmograph, the pulse-oxy meter type sphygmograph which can be mounted on the tip of the finger or the earlobe or the acceleration type sphygmograph which can be mounted on the tip of the finger does not oppose the x-raying.

The heartbeat phase of the object 5 detected by the electrocardiograph or the sphygmograph is digitized and input into the control means 41 in real time. For this purpose, the x-ray tube is moved to the positions S1, S2, . . . Sn in sequence with the electrocardiograph or the sphygmograph mounted on the object 5 when taking the x-ray images.

At the timing at which the heartbeat phase becomes the same in each of the positions S1, S2, . . . Sn, an x-ray image of the object 5 is taken. However, there is a time lag between the time at which the heart actually shrinks and the time at which the electrocardiograph or the sphygmograph detects the shrinkage of the heart and accordingly, the time lag caused when the sensor of the electrocardiograph is mounted, for instance, on the arm of the object 5 or when the sphygmograph is mounted, for instance, on the tip of the finger is measured in advance and the actual heartbeat phase is estimated on the basis of the time lag. Further, since there is a time lag between the time the x-ray apparatus 2 receives the X-ray generating signal and the time the x-ray source actually discharges x-rays, the control means 41 outputs the X-ray generating signal to the x-ray apparatus 2 taking into account the time lag.

When the heartbeat phase becomes a predetermined phase in the position S1 of the x-ray tube, the control means 41 outputs the X-ray generating signal to the x-ray apparatus 2 to take an x-ray image of the object 5. The taken x-ray image of the chest of the object 5 is transmitted to the computer 4 from the x-ray apparatus 2 and stored in the image storage means 42.

After the image taking in the position S1 of the x-ray tube, the x-ray tube is moved to the position S2 and the heartbeat phase of the object 5 is detected. When the detected heartbeat phase becomes equal to that when the x-ray image was taken in the position S1, the control means 41 outputs the X-ray generating signal to the x-ray apparatus 2 to take another x-ray image of the object 5. Similarly, when the x-ray tube is moved to the positions S1, S2, . . . Sn, an x-ray image of the object 5 is taken at the timing at which the heartbeat phase detected by the heartbeat phase detecting system 3 in each position becomes the same as that when the x-ray image was taken in the position S, and the x-ray images 100 thus taken are stored in the image storage means 42.

Otherwise, the images 100 thus obtained may be once stored in another storage medium (for instance, a portable memory such as a DVD or a file server) and then transferred to the image storage means 42.

In the tomogram obtaining means 43, a tomogram 200 of the object 5 at a necessary cross-section is obtained by adjusting the positions of the x-ray images 100 taken in the same heartbeat phases according to the position of the necessary cross-section and adding up the x-ray images 100.

As can be understood from the description above, by obtaining a tomogram from x-ray images taken in the same heartbeat phases, a light shadow such as of lung cancer near the heart does not disappear in the tomogram due to influence of the heart motion (motion artifact) and the chest can be observed in detail.

A radiation image recording system in accordance with a second embodiment of the present invention will be described, hereinbelow. In the second embodiment, a case where the x-ray images are taken with the object 5 naturally breathing without holding his or her breath will be described. Further, in this embodiment, the elements analogous to those in the preceding embodiment are given the same reference numerals and will not be described in detail.

Figure 3:
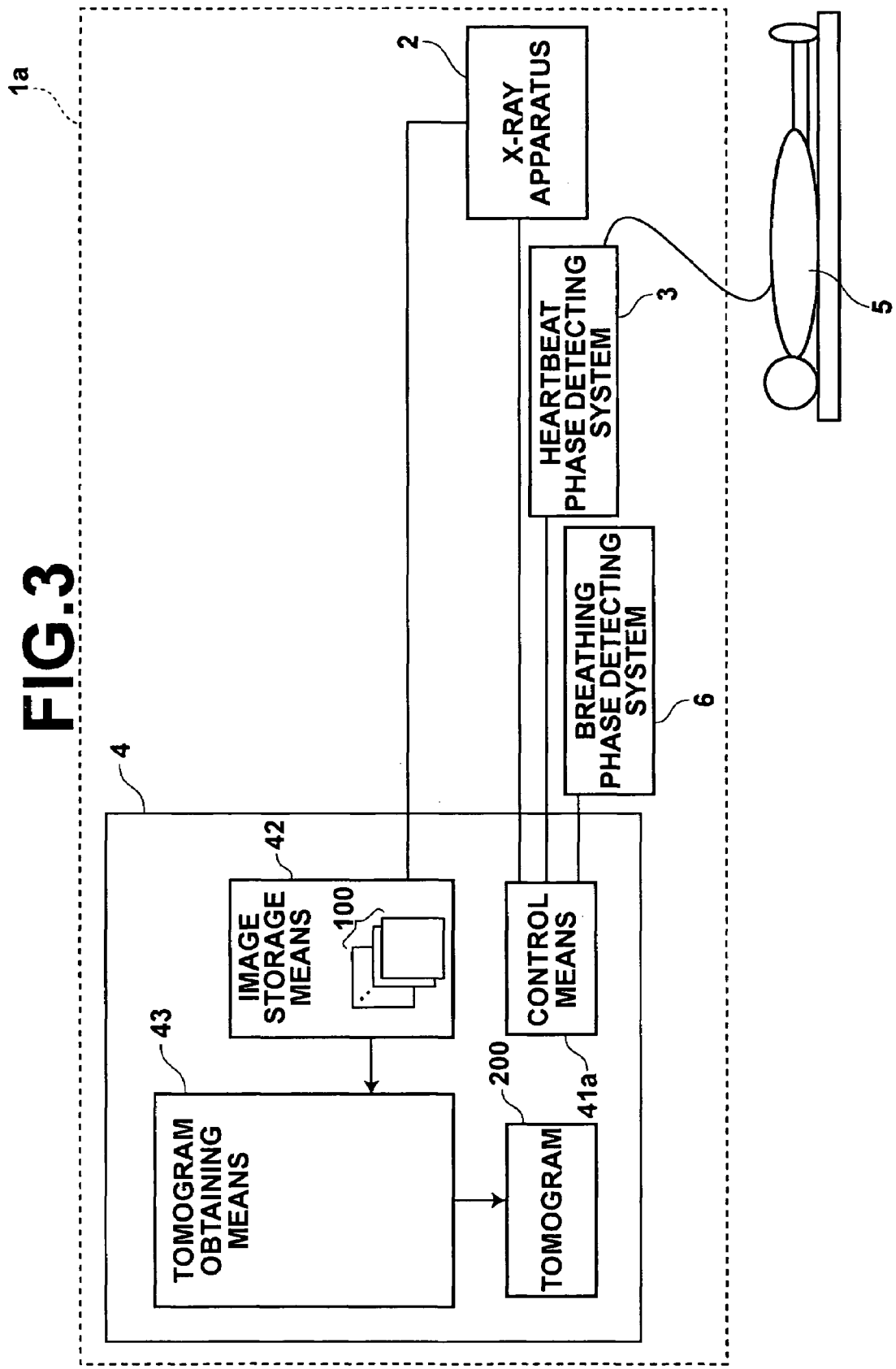
FIG. 3 is a schematic view showing a basic arrangement of a radiation image recording system in accordance with a second embodiment of the present invention.

As shown in FIG. 3, the radiation image recording system 1a in accordance with the second embodiment of the present invention comprises an x-ray apparatus (tomosynthetic image taking apparatus) 2 such as CR which takes an x-ray image of an object 5 in each of a plurality of positions of an x-ray source, a heartbeat phase detecting system (heartbeat phase detecting means) 3 which detects the heartbeat phase of the object 5, a breathing phase detecting system (breathing phase detecting means) 6 which detects the breathing phase of the object 5, and a computer 4 which controls the image taking timing of the x-ray apparatus 2.

The computer 4 comprises a control means 41a which controls the image taking timing of the x-ray apparatus 2, an image storage means 42 which stores the x-ray image 100 taken by the x-ray apparatus 2 in each of the plurality of positions of the x-ray source, and a tomogram obtaining means 43 which obtains a tomogram 200 of the object 5 by adjusting the positions of the x-ray images 100 according to the depth of a necessary cross-section and adding up the x-ray images 100.

The control means 41a is connected to the heartbeat phase detecting system 3 and the breathing phase detecting system 6 to receive the heartbeat phase and the breathing phase of the object 5 in real time and makes an instruction of taking an x-ray image of the object 5 by outputting an X-ray generating signal to the x-ray apparatus 2 in the same heartbeat phase and in the same breathing phase of the object 5 when the x-ray tube thereof is in each of the positions S1, S2, . . . Sn.

The breathing phase detecting system 6 is a system for detecting the breathing phase of the object 5. The breathing phase of the object may be detected, for instance, by observing the motion of the chest of the object to monitor breathing of the object by the use of a spirometer, a breathing monitor belt and/or an optical camera and the breathing phase detecting system 6 digitizes the analog signal thus obtained and outputs the digital signal to the control means 41a in real time.

In order to take x-ray images 100 of the chest of the object 5 for obtaining a tomosynthetic image in the same heartbeat phase and in the same breathing phase in each of the plurality of positions of the x-ray source, the heartbeat phase and the breathing phase of the object 5 must be detected. For this purpose, the heartbeat phase detecting system 3 and the breathing phase detecting system 6 are mounted on the object 5.

The control means 41a receives the heartbeat phase and the breathing phase of the object 5 in real time respectively from the heartbeat phase detecting system 3 and the breathing phase detecting system 6 and makes an instruction of taking an x-ray image of the object 5 by outputting an X-ray generating signal to the x-ray apparatus 2 in the same heartbeat phase and in the same breathing phase of the object 5 when the x-ray tube thereof is in each of the positions S1, S2, . . . Sn.

As in the case of the heartbeat phase, there is sometimes a time lag between the actual breathing phase and the detected breathing phase. Accordingly, it is preferred that the time lag to be caused be measured in advance and the x-ray image be taken according to an estimation of the actual breathing phase estimated on the basis of the time lag.

Then x-ray images are taken with the x-ray tube moved to the positions S1, S2, . . . Sn in sequence as in the preceding embodiment and at the timing at which the heartbeat phase and the breathing phase become the same in each of the positions S1, S2, . . . Sn of the x-ray tube. In the tomogram obtaining means 43, a tomogram 200 of the object 5 at a necessary cross-section is obtained by adjusting the positions of the x-ray images 100 taken in the same heartbeat phases and in the same breathing phases according to the position of the necessary cross-section and adding up the x-ray images 100.

Though, in the above description, the breathing phase is detected by the use of the breathing phase detecting system 6, it is possible to evaluate in real time chest x-ray images taken by scanning the chest with a small dose of x-rays from the x-ray apparatus 2 to obtain the breathing phase, and to transmit the breathing phase thus obtained to the control means 41$a$.

As can be understood from the description above, by obtaining a tomogram from x-ray images taken in the same heartbeat phases and in the same breathing phases, a light shadow such as of lung cancer near the heart does not disappear in the tomogram due to influence of the heart motion (motion artifact) and the chest can be observed in detail.

Though, in the first and second embodiments described above, an x-ray apparatus and a computer separate from the x-ray apparatus form a radiation image recording apparatus, the means which are formed by the computer may be built in the x-ray apparatus.

Figure 4:
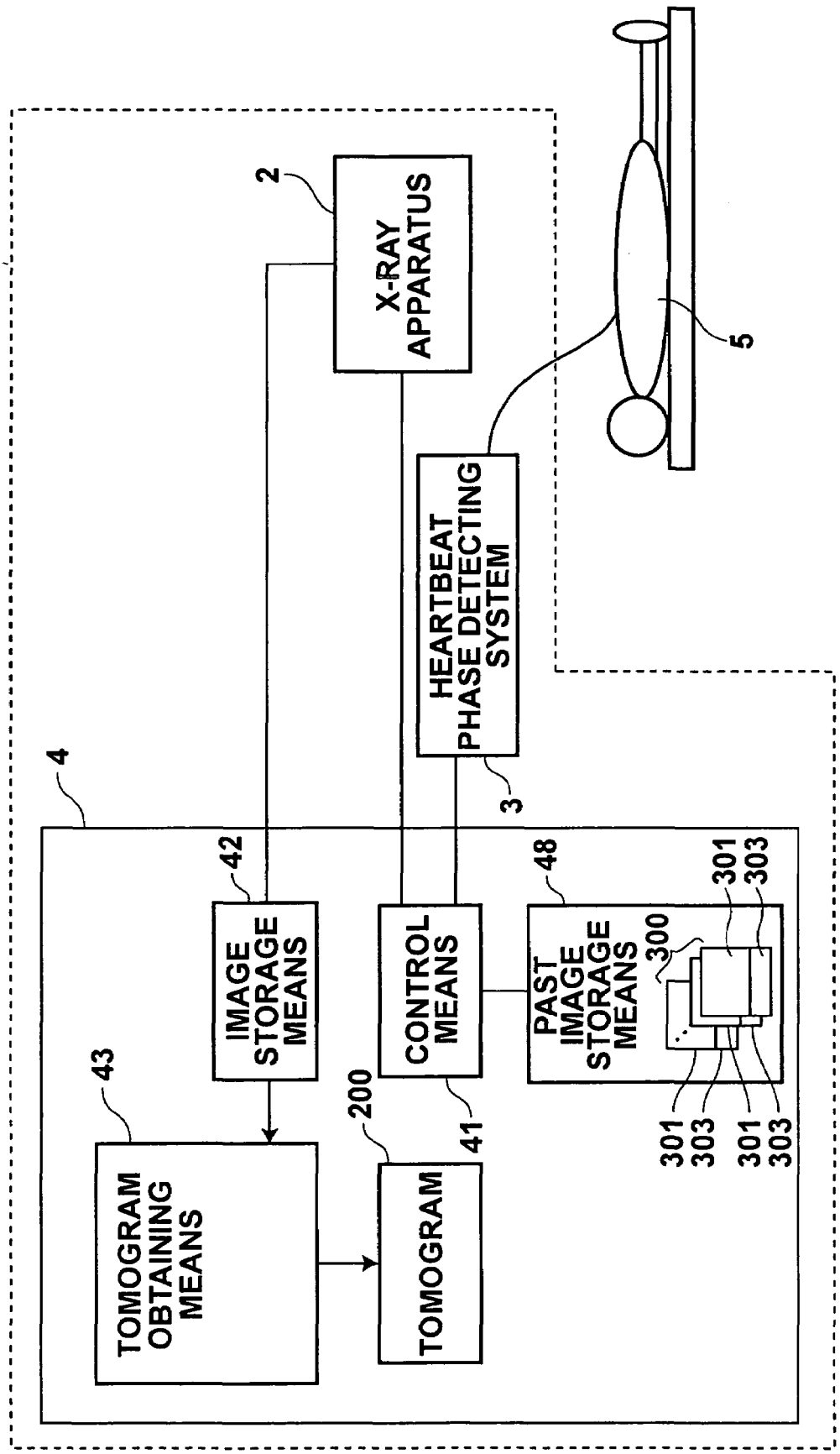
FIG. 4 is a view for illustrating an arrangement when x-ray images are taken in synchronization of the heartbeat phases in the past x-ray images.
Figure 5:
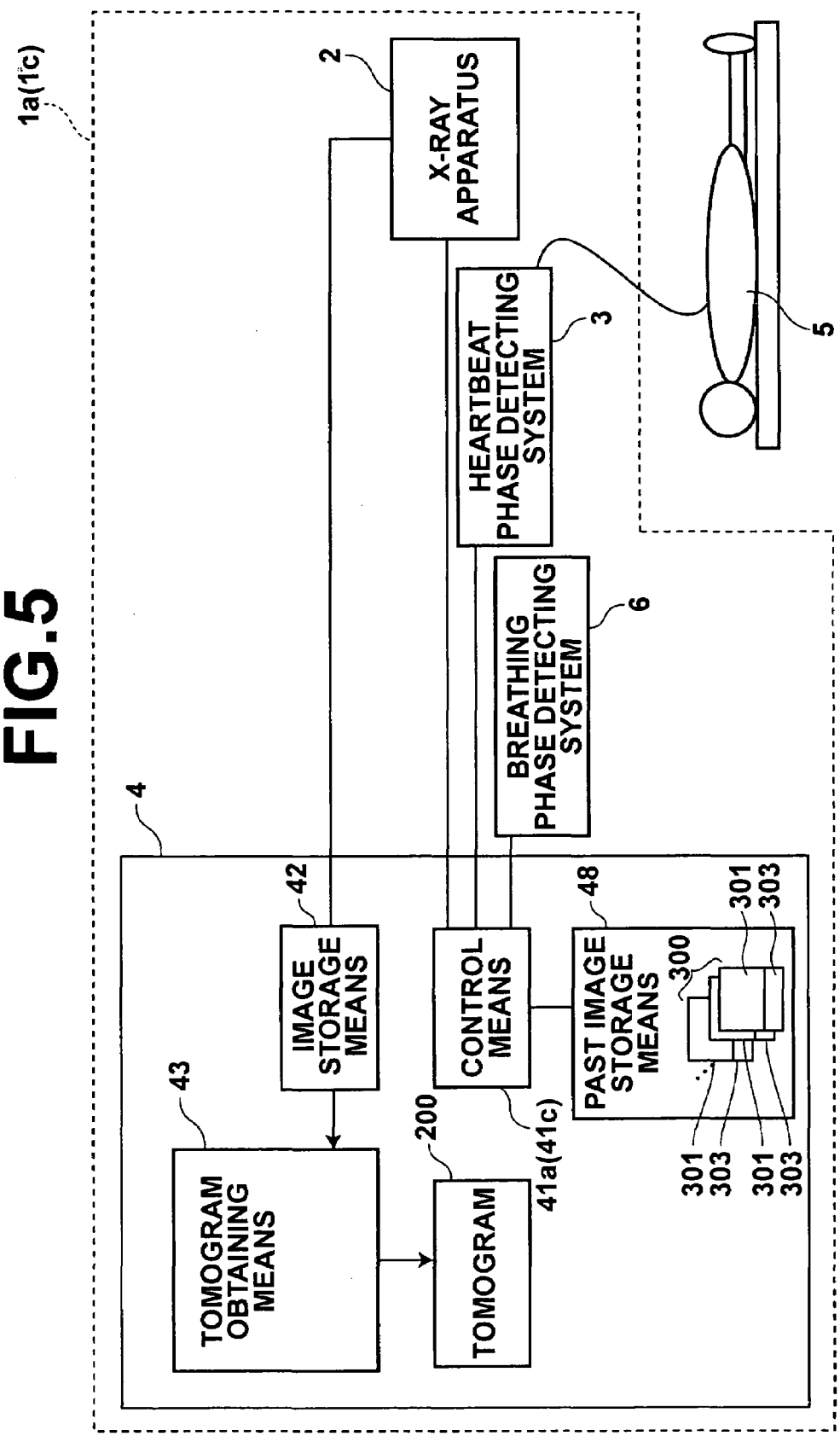
FIG. 5 is a view for illustrating another arrangement when x-ray images are taken in synchronization of the heartbeat phases in the past x-ray images.

Further, though, in the first and second embodiments described above, x-ray images are taken in the same heartbeat phase in each of the positions S1, S2, . . . Sn of the x-ray tube, the radiation image recording apparatus of the present invention may further comprise a past image storage means 48 as shown in FIG. 4 or 5 so that the past image storage means 48 stores a plurality of x-ray images 301 which were taken for obtaining the tomosynthetic image in the past in the same heartbeat phase together with heartbeat information 303 on the heartbeat phase at the time the x-ray images 301 were taken, and the control means 41 (or 41$a$) outputs the X-ray generating signal to the x-ray apparatus 2 to take the x-ray image when the heartbeat phase becomes equal to that of the image stored in the past image storage means 48 in each of the positions S1, S2, . . . Sn of the x-ray tube. The images 301 with the heartbeat information 303 will be sometimes referred to as the "images 300" hereinbelow.

By taking the x-ray images in the heartbeat phase equal to that of the past images, a subtraction tomogram representing the difference between a past tomogram which is created on the basis of the past x-ray images for obtaining the tomosynthetic image, and a current tomogram which is created on the basis of the current x-ray images for obtaining the tomosynthetic image can be obtained, whereby the diseased part can be observed in detail. Especially, a light shadow such as of lung cancer near the heart sometimes cannot be observed in the subtraction tomogram due to influence of the heart motion, whereas, when the x-ray images are taken in the heartbeat phase equal to that of the past images, even such a light shadow can be observed in the subtraction tomogram.

Further, when a subtraction tomogram representing the difference between the past x-ray images which were taken without contrast agent and the current x-ray images which are taken with contrast agent is obtained, the structure in the background can be removed to obtain an image of the area which has been taken with contrast agent.

When a contrast agent distribution map is created by adding up the areas which have been taken with contrast agent obtained by the subtraction images and an image where a contrast agent distribution is enhanced is generated by superimposing the contrast agent distribution map on one of the past x-ray images, comparison of the object with the structure is facilitated.

A radiation image recording apparatus in accordance with a third embodiment of the present invention will be described, hereinbelow. In the radiation image recording apparatus in accordance with the third embodiment of the present invention, the plurality of x-ray images for the tomosynthesis are corrected so that they are in the same heartbeat phase and then the tomogram is obtained from the x-ray images. In this embodiment, it is assumed that the images are taken with the object 5 holding his or her breath after he or she takes a large breath to inflate the lung. Further, in this embodiment, the elements analogous to those in the preceding embodiments are given the same reference numerals and will not be described in detail.

As shown in FIG. 6, the radiation image recording system 1$b$ in accordance with the third embodiment of the present invention comprises an x-ray apparatus (tomosynthetic image taking apparatus) 2 such as CR which takes an x-ray image of an object 5 in each of a plurality of positions of an x-ray source, a heartbeat phase detecting system (heartbeat phase detecting means) 3 which detects the heartbeat phase of the object 5, and a computer 4 which controls the image taking timing of the x-ray apparatus 2.

The computer 4 comprises a control means 41 which controls the image taking timing of the x-ray apparatus 2, and an image processing system (image processing means) 40 which obtains a tomogram 200 from the x-ray images 100 taken by the x-ray apparatus 2.

The image processing system 40 comprises an image storage means 42 which stores the x-ray image 100 taken by the x-ray apparatus 2 in each of the plurality of positions of the x-ray source, a correction means 46 which corrects each of the x-ray images 100 so that they are all in the same heartbeat phase, and a tomogram obtaining means 43 which obtains a tomogram 200 by adjusting the positions of the x-ray images 100 according to the depth of a necessary cross-section and adding up the x-ray images 100.

Since the shape of the lung changes depending on the heartbeat phase at the part of the lung near to the heart and the lung image is taken in an expanded shape at the part of the lung near to the heart when the heart shrinks whereas in a compressed shape at the part of the lung near to the heart when the heart expands, a light shadow such as of lung cancer near the heart cannot be enhanced even if the positions of the x-ray images 100 adjusted and then the x-ray images 100 are added up. A light shadow such as of lung cancer can be enhanced by obtaining tomogram 200 by correcting each of the x-ray images 100 so that they are all in the same heartbeat phase and by the use of the corrected x-ray images 100.

Figure 7A:
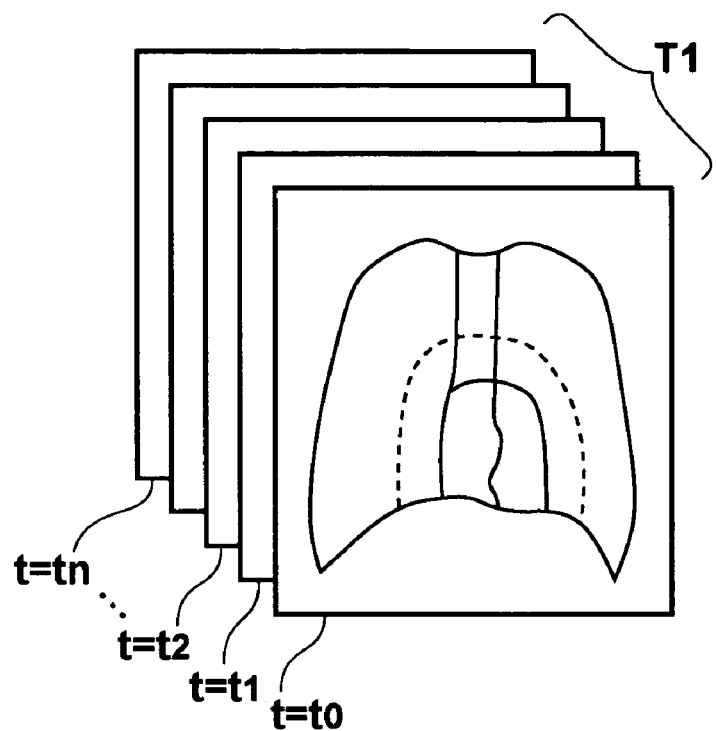
FIGS. 7A and 7B are views for illustrating a template according to the heartbeat phase.
Figure 7B:
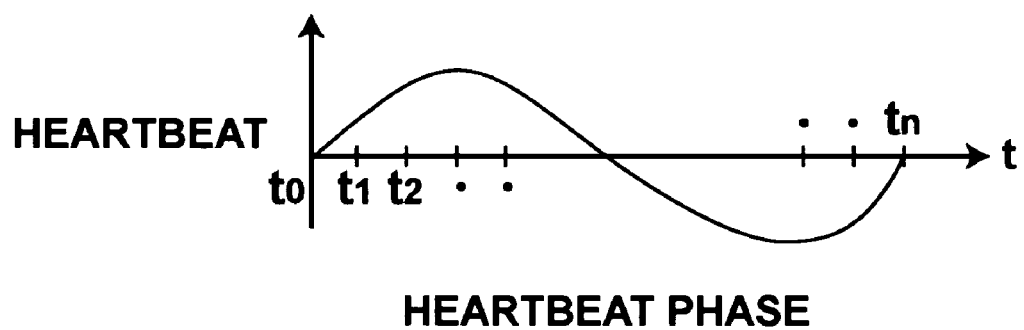

In order to correct the phase of the taken images, the image of the object is continuously taken object by object with a small dose of x-rays, at the beginning of observing the change with time of the diseased part of the object, to obtain a plurality of images in different heartbeat phases, and a plurality of templates T1 corresponding to the heartbeat phases (FIG. 7B) are created as shown in FIG. 7A. The templates T1 should be created at sufficiently short intervals so that an image corresponding to the taken image in the heartbeat phase can be surely obtained.

Figure 8:
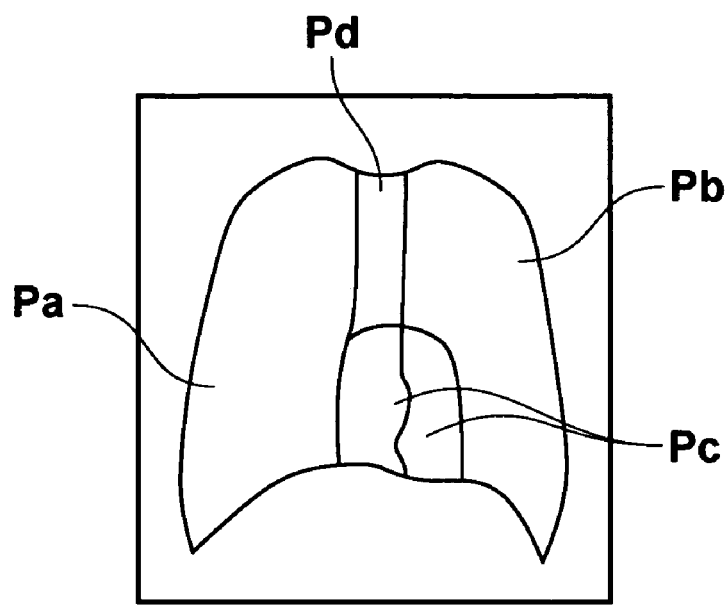
FIG. 8 is a view for illustrating the areas of the chest.
Figure 9:
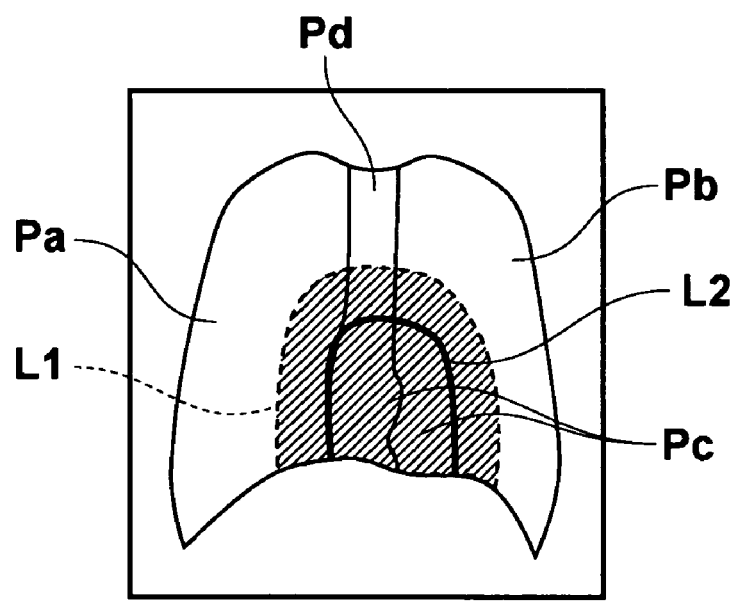
FIG. 9 is a view for illustrating the areas of the lung changing in response to the motion of the heart.

The lung largely changes in response to motion of the heart at the part near to the heart but is not affected by motion of the heart at the part remote from the heart. Accordingly, from each of the templates T1, areas such as a lung area (Pa and Pb shown in FIG. 8), a mediastinum area (Pd), a heart area (Pc) and the like are extracted (described in detail in Japanese Unexamined Patent Publication No. 2003-006661), and a part of the lung within a predetermined range from the heart area is defined to be a changing area (hatched portion in FIG. 9) which changes depending on the heartbeat phase on the basis of data empirically obtained from the images. For example, the changing area is set to be about twice the heart area. On the outer periphery L1 of the changing area (shown by the broken line in FIG. 9), the shape of the lung hardly changes with change in the heartbeat phase and the rate of change is about 0. On the outer periphery L2 of the heart area, the shape of the lung changes most in response to motion of the heart, and the rate of change in the shape of the lung gradually decreases from the outer periphery L2 of the heart area toward the outer periphery L1 of the changing area.

Accordingly, in order to deform the image in the heartbeat phase t1 (FIG. 10A) to the image in the heartbeat phase t2 (FIG. 10B), the pixels on the outer periphery L2 of the heart area in the heartbeat phase t1 are warped to coincide with those on the outer periphery L2 of the heart area in the heartbeat phase t2 and the pixels included in the changing area of the image in the heartbeat phase t1 are warped to the positions of the pixels included in the changing area of the image in the heartbeat phase t2 so that the rate of change in the position of the pixels gradually decreases from the outer periphery L2 of the heart area toward the outer periphery L1 of the changing area and the pixels on the outer periphery L1 of the changing area are kept stationary (FIG. 10C).

When all the images 100 are to be, for instance, in a maximum shrink phase where the heart shrinks most, the correction means 46 extracts the lung area (Pa and Pb), the mediastinum area (Pd), the heart area (Pc) and the like from each image 101 of the x-ray images 100 and then extracts the changing area by the use of the templates T1 corresponding to the heartbeat phases of each image 101. Then the correction means 46 warps the pixels in the changing area to the position in the template T1 corresponding to the maximum shrink phase in each image 101, thereby correcting all the images 101 in the images 100 to images in the maximum shrink phase.

The tomogram obtaining means 43 obtains a tomogram 200 in a necessary cross-section by adjusting the positions of the x-ray images 100 corrected to the template corresponding to the maximum shrink phase and adding up the corrected x-ray images 100 as in the preceding embodiments.

Though the case where all the images 101 in the images 100 are corrected to be in the maximum shrink phase has been described in this embodiment, the images 101 in the images 100 may be corrected to be in another heartbeat phase so long as they are all in the same heartbeat phase.

As can be understood from the description above, even if the x-ray images taken are not in the same heartbeat phase, a light shadow such as of lung cancer near the heart does not disappear in the tomogram due to influence of the heart motion (motion artifact) and the chest can be observed in detail by creating the tomogram after correcting the images to be in the same heartbeat phase.

A radiation image recording system in accordance with a fourth embodiment of the present invention will be described, hereinbelow. In the fourth embodiment, a case where, though taken with the object 5 naturally breathing without holding his or her breath as in the second embodiment, the x-ray images are taken when the heartbeat phase becomes the same in each of the positions will be described. Further, in this embodiment, the elements analogous to those in the preceding embodiments are given the same reference numerals and will not be described in detail.

As shown in FIG. 11, the radiation image recording system 1c in accordance with the fourth embodiment of the present invention comprises an x-ray apparatus (tomosynthetic image taking apparatus) 2 such as CR which takes an x-ray image of an object 5 in each of a plurality of positions of an x-ray source, a heartbeat phase detecting system (heartbeat phase detecting means) 3 which detects the heartbeat phase of the object 5, a breathing phase detecting system (breathing phase detecting means) 6 which detects the breathing phase of the object 5, and a computer 4 which controls the image taking timing of the x-ray apparatus 2.

The computer 4 comprises a control means 41c which controls the image taking timing of the x-ray apparatus 2, an image storage means 42 which stores the x-ray image 100 taken by the x-ray apparatus 2 in each of the plurality of positions of the x-ray source, and a tomogram obtaining means 43 which obtains a tomogram 200 of the object 5 by adjusting the positions of the x-ray images 100 according to the depth of a necessary cross-section and adding up the x-ray images 100.

The control means 41c is connected to the heartbeat phase detecting system 3 to receive the heartbeat phase the object 5 in real time and makes an instruction of taking an x-ray image of the object 5 by outputting an X-ray generating signal to the x-ray apparatus 2 in the same heartbeat phase and in the same breathing phase of the object 5 when the x-ray tube thereof is in each of the positions S1, S2, . . . Sn. Further, the breathing phase detecting system 6 is connected to the control means 41c, and the control means 41c stores in the computer the breathing phase when an x-ray image is taken in each of the positions S1, S2, . . . Sn as breath information 102 for the corresponding x-ray image.

Figure 12A:
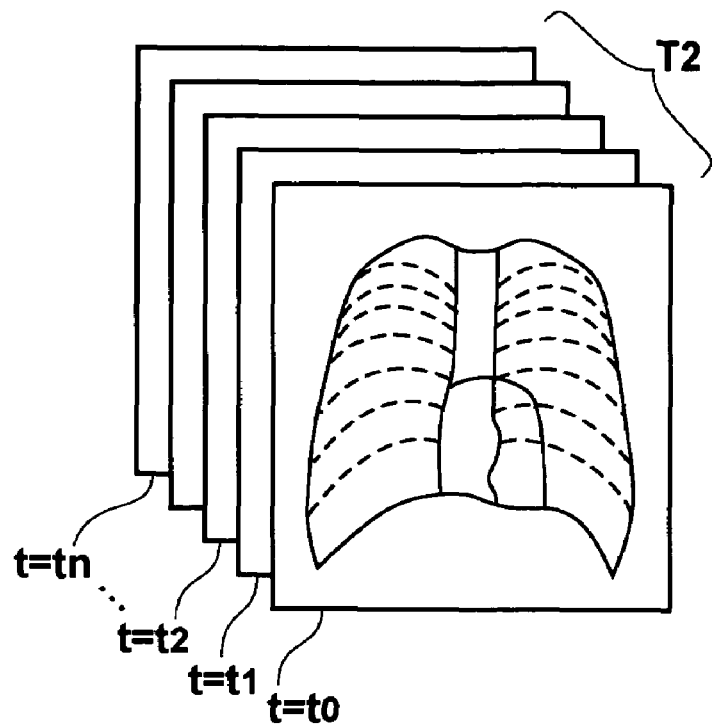
FIGS. 12A and 12B are views for illustrating a template according to the breathing phase.
Figure 12B:
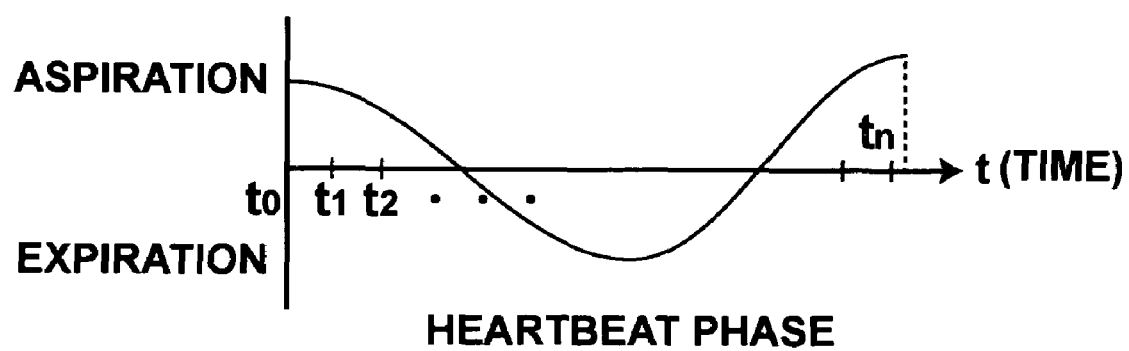

As in the third embodiment, the image of the object is continuously taken object by object with a small dose of x-rays to obtain a plurality of images in different heartbeat phases from those which are substantially in the same heartbeat phase, and a plurality of templates T2 corresponding to the heartbeat phases (FIG. 12B) are created as shown in FIG. 12A. On the basis of this templates T2, the images are corrected.

Since the ribs and/or the diaphragm move and down depending on the breathing phase, and the position of the lung moves in response to the motion of the ribs and/or the diaphragm. Accordingly, from each of the templates T2, areas such as a lung area (Pa and Pb shown in FIG. 8), a mediastinum area (Pd), a heart area (Pc) and the like and the ribs are extracted, and the lung area is warped so that the positions of the mediastinum area, the ribs, the outer periphery of the lung area and the lower portion of the lung area (the diaphragm) coincide with each other.

Then the correction means 46 extracts the lung area (Pa and Pb), the mediastinum area (Pd), the heart area (Pc) and the like and the ribs from each image 101 of the x-ray images 100. Further, as shown in FIGS. 13A to 13C, the correction means 46 warps the pixels in the lung area to the position in the template T2 corresponding to the maximum expiration phase (FIG. 13A) on the basis of the breathing phases represented by the breath information, thereby correcting all the images 101 in the images 100 to images in the maximum expiration phase (FIG. 13C).

The tomogram obtaining means 43 obtains a tomogram 200 in a necessary cross-section by adjusting the positions of the x-ray images 100 corrected to those in the maximum expiration phase and adding up the corrected x-ray images 100 as in the preceding embodiments.

Though the case where all the images 101 in the images 100 are corrected to be in the maximum expiration phase has been described in this embodiment, the images 101 in the images 100 may be corrected to be in another breathing phase so long as they are all in the same breathing phase.

As can be understood from the description above, even if the x-ray images taken are not in the same breathing phase though in the same heartbeat phase, a light shadow such as of lung cancer does not disappear in the tomogram under influence of the lung motion due to breathing (motion artifact) and can be observed in detail by creating the tomogram after correcting the images to be in the same breathing phase.

The case where the x-ray images are taken in the positions S1, S2, . . . Sn of the x-ray tube in the same heartbeat phase has been described above in conjunction with the first and second embodiments of the present invention. However it is possible that the radiation image recording apparatus is provided with a past x-ray image storage means 48 which stores a plurality of x-ray images 301 (sometimes referred to as the "x-ray image 301 of the x-ray image group 300") which were taken for obtaining the tomosynthetic image in the past in the same heartbeat phase, and the past x-ray image storage means 48 is caused to store the x-ray images 301 together with heartbeat information 303 on the heartbeat phase at the time the x-ray images 301 were taken, and the control means outputs an X-ray generating signal to the x-ray apparatus 2 to take an x-ray image of the object 5 when the heartbeat phase becomes the same as that stored in the past x-ray image storage means 48 in each of the positions S1, S2, . . . Sn.

By thus taking the x-ray images in the heartbeat phase synchronized with the heartbeat phase at which the past x-ray images were taken, a subtraction image between the past tomogram obtained by the past x-ray images and a current tomogram obtained by the current x-ray images can be obtained and change of the diseased part can be accurately observed.

Further, when the past x-ray images were taken without contrast agent and the current x-ray images are taken with contrast agent, the structure in the background can be removed and an image of the area which has been taken with contrast agent can be obtained. Further, when a contrast agent distribution map is created and a contrast agent distribution enhanced image is generated by superimposing the contrast agent distribution map on one of the past x-ray images, comparison of the object with the structure is facilitated.

A radiation image recording apparatus in accordance with a fifth embodiment of the present invention will be described, hereinbelow. In the radiation image recording apparatus in accordance with the fifth embodiment of the present invention, a case where the x-ray images are taken with the object 5 naturally breathing without holding his or her breath and the x-ray images for the tomosynthesis are corrected so that they are in the same heartbeat phase and in the same breathing phase before the tomogram is obtained will be described. Further, in this embodiment, the elements analogous to those in the preceding embodiments are given the same reference numerals and will not be described in detail.

Figure 14:
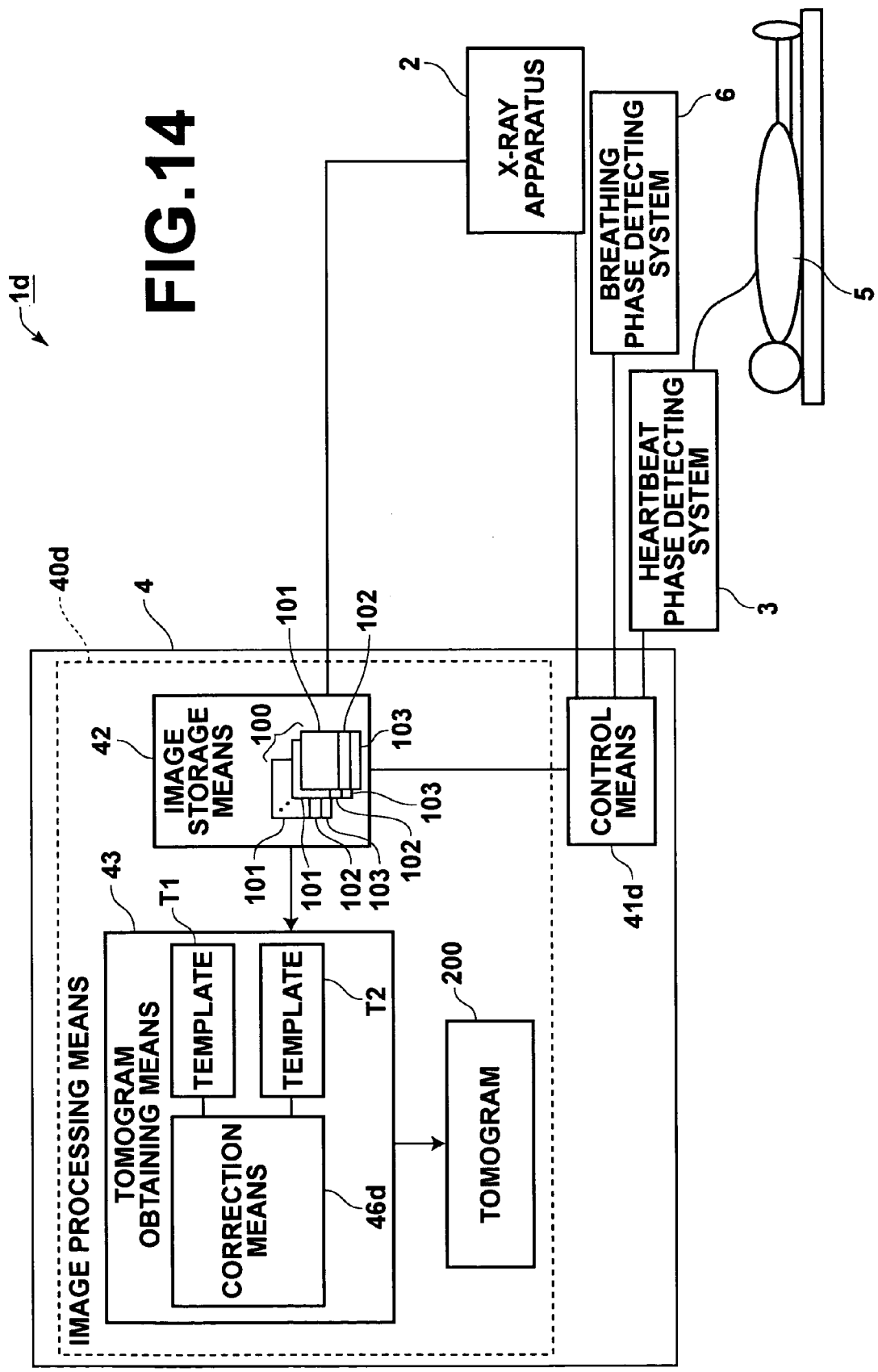
FIG. 14 is a schematic view showing a basic arrangement of a radiation image recording system in accordance with a fifth embodiment of the present invention.

As shown in FIG. 14, the radiation image recording system 1$d$ in accordance with the fifth embodiment of the present invention comprises an x-ray apparatus (tomosynthetic image taking apparatus) 2 such as CR which takes an x-ray image of an object 5 in each of a plurality of positions of an x-ray source, a heartbeat phase detecting system (heartbeat phase detecting means) 3 which detects the heartbeat phase of the object 5, a breathing phase detecting system (breathing phase detecting means) 6 which detects the breathing phase of the object 5 and a computer 4 which controls the image taking timing of the x-ray apparatus 2.

The computer 4 comprises a control means 41 which controls the image taking timing of the x-ray apparatus 2, and an image processing system (image processing means) 40$d$ which obtains a tomogram from the x-ray images taken by the x-ray apparatus 2.

The image processing system 40$d$ comprises an image storage means 42 which stores the x-ray image 100 taken by the x-ray apparatus 2 in each of the plurality of positions of the x-ray source, a correction means 46 which corrects each of the x-ray images 100 so that they are all in the same heartbeat phase and in the same breathing phase, and a tomogram obtaining means 43 which obtains a tomogram by adjusting the positions of the x-ray images 100 according to the position of a necessary cross-section and adding up the x-ray images 100.

The control means 41$d$ is connected to the heartbeat phase detecting system 3 and to the breathing phase detecting system 6 and stores in the computer the breathing phase and the heartbeat phase when an x-ray image is taken in each of the positions S1, S2, . . . Sn as breath information 102 and heartbeat information 103 for the corresponding x-ray image.

As in the third and fourth embodiments, the image of the object is continuously taken object by object with a small dose of x-rays to obtain a plurality of images in different heartbeat phases in which the breathing phases are in the same breathing phase and a plurality of images in different breathing phases in which the heartbeat phases are in the same heartbeat phase, and a plurality of templates T1 and T2 are created.

The correction means 46$d$ first corrects the images 101 of the image group 100 to images in the maximum expiration phase by the use of the templates T2 as in the fourth embodiment.

Then the correction means 46$d$ corrects the images 101 of the image group 100 corrected to those in the maximum expiration phase to images in the same heartbeat phase with the past x-ray images by the use of the templates T1 as in the third embodiment.

The tomogram obtaining means 43 obtains a tomogram by adjusting the positions of the x-ray images 100 corrected to those in the same heartbeat phase and in the same breathing phase and adding up the corrected x-ray images 100 as in the preceding embodiments.

As can be understood from the description above, even if the x-ray images taken are neither in the same breathing phase nor in the same heartbeat phase, a light shadow such as of lung cancer does not disappear in the tomogram under influence of the heart motion or the lung motion due to breathing (motion artifact) and can be enhanced by creating the tomogram after correcting the images to be in the same heartbeat phase and in the same breathing phase.

Though, in the third to fifth embodiments described above, the case where the images are corrected by the use of the templates discrete to the objects is described above, the images may be corrected by extracting areas such as a lung area, a mediastinum area, a heart area and the like for each heartbeat phase from a number of images and warping the pixels in the lung area by distances corresponding to the empirically obtained average rate of change of the pixels in the lung area in the case where the templates are not prepared in advance. For example, the rate of change of the outer periphery of the heart area which changes with the heartbeat phase may be obtained as the rate of change of the distance from the center of gravity of the heart area.

Similarly, as for the breathing phase, the images may be corrected by warping the pixels in the lung area by distances corresponding to the empirically obtained average rate of change of the pixels in the lung area in the case where the templates are not prepared in advance.

Though, in the third and fifth embodiments described above, the computer is connected to the x-ray apparatus, the heartbeat phase detecting means and the like, the computer may be provided with only the image processing means and the image storage means in place of connecting the computer to the x-ray apparatus, the heartbeat phase detecting means and the like so that the past images and/or the current images are read from a portable storage medium such as a DVD. Otherwise, a computer provided with only the image processing means and the image storage means may be connected by way of a network to a file server in which the past images and/or the current images are stored so that the images stored in the file server are read out to the computer.

Further, the x-ray apparatus may be provided with each means which is formed by a computer also in the third and fifth embodiments described above.

Further, though in the embodiments described above, the heartbeat phase as detected by the heartbeat phase detecting means is stored as the heartbeat information, the heartbeat information may be obtained by extracting the heart area from the images and detecting the heartbeat phase on the basis of the size and/or the shape of the heart area. Similarly, the breathing information may be obtained by extracting the chest area from the images and detecting the breathing phase on the basis of the size and/or the shape of the chest area in place of storing the information detected by the breathing phase detecting means as the breath information. For example, a detector such as an FPD can be used for the purpose.

In the embodiments described above, a scattering radiation removing grid which is positioned between the object 5 and a detecting surface such as an imaging plate to suppress scattering radiation from entering may be used when taking the image of the object 5 by the x-ray apparatus 2. A typical scattering radiation removing grid comprises a number of lead foil (radiation-shielding material) sheets which are laminated spaced from each other in parallel to the radiation from an x-ray source. When an image is taken by the use of such a scattering radiation removing grid, an image on which the image of the layer structure of the scattering radiation removing grid is superimposed is obtained.

Figure 15:
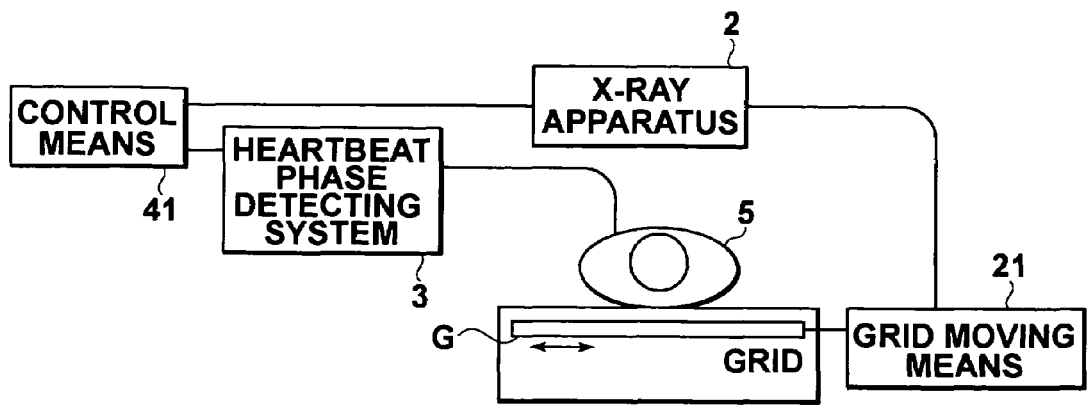
FIG. 15 is a view for illustrating an arrangement when x-ray images are taken by the use of a scattering radiation removing grid.
Figure 16:
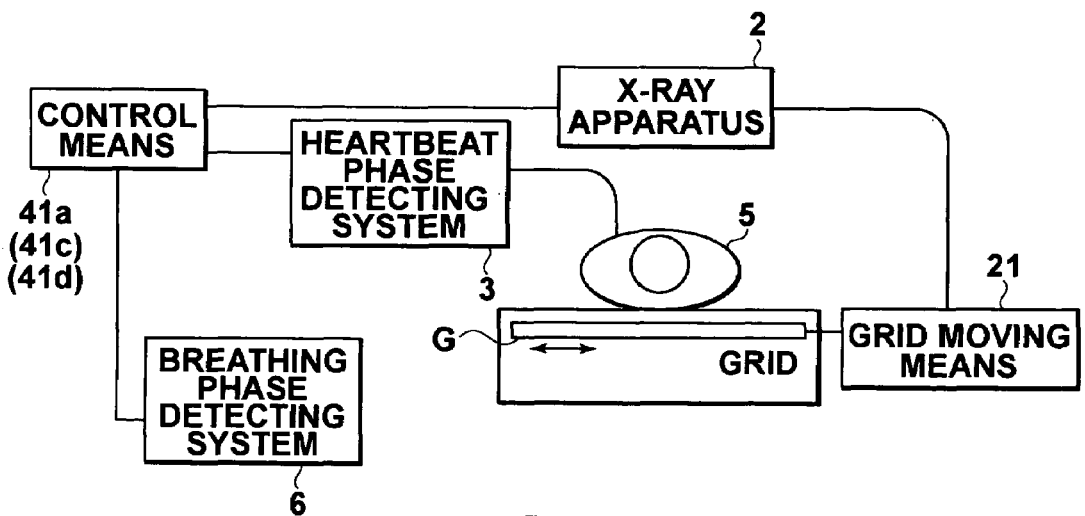
FIG. 16 is a view for illustrating another arrangement when x-ray images are taken by the use of a scattering radiation removing grid.

In order to avoid this, the x-ray apparatus 2 is provided with a grid moving mechanism (a grid moving means) 21 for moving back and forth the scattering radiation removing grid G in a direction transverse to its layer structure to blur the image thereof while x-rays are projected as shown in FIG. 15 or 16. Since the image of the scattering radiation removing grid G is more blurred as the distance by which the scattering radiation removing grid G is moved while x-rays are projected increases, it is preferred that the moving speed of the scattering radiation removing grid G be maximized within the time for which x-rays are projected. Accordingly, the grid moving means 21 is connected to the control means 41 (41a, 41c, 41d) and the control means 41 (41a, 41c, 41d) controls the grid moving means 21 so that the moving speed of the scattering radiation removing grid G is maximized at the timing at which the X-ray generating signal is output to the x-ray apparatus 2.

In order to support the physical structure of the grid G, interstices of the scattering radiation removing grid G are packed with radiation transmitting material such as wood or aluminum. Since the grid moving means 21 mechanically moves back and forth the scattering radiation removing grid G, the moving speed of the scattering radiation removing grid G is not maximized at the turn. Accordingly, for instance, a synchronization signal which synchronizes with the heartbeat phase (or the breathing phase) detected by the control means 41 (41a, 41c, 41d) is transmitted to the grid moving means 21 to control the movement of the scattering radiation removing grid G so that the moving speed of the scattering radiation removing grid G is maximized synchronized with the S heartbeat phase (or the breathing phase) in which the x-ray images are taken. Otherwise, the control means 41 (41a, 41c, 41d) may transmits a start signal, which starts the movement of the scattering radiation removing grid G, to the grid moving means 21 so that the moving speed of the scattering radiation removing grid G is maximized when the heartbeat phase (or the breathing phase) becomes the phase in which the x-ray images are to be taken.

When the x-ray images are taken without moving the scattering radiation removing grid G, an image on which the image of the layer structure of the scattering radiation removing grid is superimposed is obtained. Accordingly, it is preferred that GPR processing (grid removing processing) be carried out on the x-ray images so that the tomogram is generated from x-ray images removed with the grid lines.

Otherwise, it is possible to make the grid unremarkable on the images by taking the images at increased density of the layers of the grid in place of moving the scattering radiation removing grid G. It is preferred at this time that the density of the grid of the scattering radiation removing grid G be not less than about 5 cyc/mm (not less than the Nyquist frequency of the read-out pixel density) in the case of a general image of the chest, and be not less than about 10 cyc/mm (not less than the Nyquist frequency of the read-out pixel density) in the case of an image of the breast or the like. That is, a high density grid equal to or beyond the minimum resolution at which the detecting unit can detect the x-ray information stored on the detecting surface such as an imaging plate or the resolution of the current images.

Further, in place of using the scattering radiation removing grid, the scattering radiation may be removed by the use of the grader method where the scattering radiation from the object is removed by positioning the detecting surface such as an imaging plate at a distance of 15 to 20 cm from the object.

By thus taking the images by the use of the scattering radiation removing grid or positioning the detecting surface such as an imaging plate apart from the object, an image which is not affected by the scattering radiation can be obtained.

Further, it is possible to record a computer program for executing functions of the computer on a computer readable storage medium such as a CD-ROM and to install it in a computer, or to install such a computer program in a computer by way of a network. A skilled artisan would know that the computer-readable medium is not limited to any specific type of storage devices and includes any kind of device, including but not limited to CDs, floppy disks, RAMs, ROMs, hard disks, magnetic tapes and internet downloads, in which computer instructions can be stored and/or transmitted. Transmission of the computer code through a network or through wireless transmission means is also within the scope of this invention. Additionally, computer code/instructions include, but are not limited to, source, object and executable code and can be in any language including higher level languages, assembly language and machine language.

What is claimed is:

1. A radiation image taking system comprising:
a tomosynthetic image taking means which takes an x-ray image of an object in each of a plurality of positions of an x-ray source to obtain a desired tomogram of the object by adding up the x-ray images thus obtained;
a heartbeat phase detecting means which detects the heartbeat phase of the object; and
a tomosynthesis control means which controls the tomosynthetic image taking means to take an x-ray image of the object in each of the plurality of positions of the x-ray source when the heartbeat of the object detected by the heartbeat phase detecting means is in the same heartbeat phase, wherein:
the tomosynthetic image taking means is provided with a scattering radiation removing grid and a grid moving means which moves the scattering radiation removing grid, and
the tomosynthesis control means controls the grid moving means so that the moving speed of the scattering radiation removing grid is maximized throughout a time in which the x-ray image of the object is taken.

2. A radiation image taking system comprising:
a tomosynthetic image taking means which takes an x-ray image of an object in each of a plurality of positions of an x-ray source to obtain a desired tomogram of the object by adding up the x-ray images thus obtained;
a heartbeat phase detecting means which detects the heartbeat phase of the object;
a tomosynthesis control means which controls the tomosynthetic image taking means to take an x-ray image of the object in each of the plurality of positions of the x-ray source when the heartbeat of the object detected by the heartbeat phase detecting means is in the same heartbeat phase; and
a breathing phase detecting means which detects the breathing phase of the object, wherein the tomosynthesis control means controls the tomosynthetic image taking means to take an x-ray image of the object in each of the plurality of positions of the x-ray source when the heartbeat of the object detected by the heartbeat phase detecting means is in the same heartbeat phase and when the breathing of the object detected by the breathing phase detecting means is in the same breathing phase.

3. A radiation image taking system as defined in claim 2 in which the tomosynthetic image taking means is provided with a scattering radiation removing grid and a grid moving means which moves the scattering radiation removing grid, and
the tomosynthesis control means controls the grid moving means so that the moving speed of the scattering radiation removing grid is maximized when the x-ray image of the object is taken.

4. A radiation image taking system comprising:
a tomosynthetic image taking means which takes an x-ray image of an object in each of a plurality of positions of an x-ray source to obtain a desired tomogram of the object by adding up the x-ray images thus obtained;
a heartbeat phase detecting means which detects the heartbeat phase of the object;
a tomosynthesis control means which controls the tomosynthetic image taking means to take an x-ray image of the object in each of the plurality of positions of the x-ray source when the heartbeat of the object detected by the heartbeat phase detecting means is in the same heartbeat phase;
a breathing phase detecting means which detects the breathing phase of the object; and
a correction means which corrects at least a part of the plurality of the images taken in the plurality of positions of the x-ray source so that they are all in the same breathing phase on the basis of the breathing phases detected by the breathing phase detecting means when the images are taken.

5. A radiation image taking system as defined in claim 4 in which the tomosynthetic image taking means is provided with a scattering radiation removing grid and a grid moving means which moves the scattering radiation removing grid, and
the tomosynthesis control means controls the grid moving means so that the moving speed of the scattering radiation removing grid is maximized when the x-ray image of the object is taken.

6. A radiation image taking system comprising
a tomosynthetic image taking means which takes an x-ray image of an object in each of a plurality of positions of an x-ray source to obtain a desired tomogram of the object by adding up the x-ray images thus obtained,
a heartbeat phase detecting means which detects the heartbeat phase of the object,
a storage means which stores the x-ray image of the object taken in each of the plurality of positions of the x-ray source, and
a correction means which corrects at least a part of the plurality of the images taken in the plurality of positions of the x-ray source so that they are all in the same heartbeat phase on the basis of the heartbeat phases detected by the heartbeat phase detecting means when the images are taken.

7. A radiation image taking system as defined in claim 6 in which
the tomosynthetic image taking means is provided with a scattering radiation removing grid and a grid moving means which moves the scattering radiation removing grid, and
the tomosynthesis control means controls the grid moving means so that the moving speed of the scattering radiation removing grid is maximized when the x-ray image of the object is taken.

8. A radiation image taking system as defined in claim 6 further comprising
a breathing phase detecting means which detects the breathing phase of the object, wherein the correction means corrects at least a part of the plurality of the images taken in the plurality of positions of the x-ray source so that they are all in the same heartbeat phase and in the same breathing phase on the basis of the heartbeat phases detected by the heartbeat phase detecting means when the image is taken and the breathing phases detected by the breathing phase detecting means when the image is taken.

9. A radiation image taking system as defined in claim 8 in which the tomosynthetic image taking means is provided with a scattering radiation removing grid and a grid moving means which moves the scattering radiation removing grid, and the tomosynthesis control means controls the grid moving means so that the moving speed of the scattering radiation removing grid is maximized when the x-ray image of the object is taken.

10. A radiation image taking system as defined in claim 6, wherein correction is performed by warping.

11. A computer-readable medium on which is recorded a computer program for causing a computer to execute the steps of reading out x-ray images of an object each of which is taken in a plurality of positions of an x-ray source and which can provide a desired tomogram of the object by adding up them, and heartbeat information representing the heartbeat phase of the object when the x-ray images are taken, and correcting at least a part of the plurality of the images taken in the plurality of positions of the x-ray source so that they are all in a same breathing phase on the basis of the breathing phases of the object when the images are taken.

12. A computer-readable medium as defined in claim 11 in which the steps further comprises steps of reading out breathing information representing the breathing phase of the object when the x-ray images are taken, wherein by the step of correcting at least a part of the plurality of the images taken in the plurality of positions of the x-ray source, at least a part of the plurality of the images taken in the plurality of positions of the x-ray source are corrected so that they are all in the same breathing phase and in the same heartbeat phase on the basis of the breathing phases and the heartbeat phases of the object when the images are taken.

* * * * *